United States Patent [19]

Eich et al.

[11] Patent Number: 5,162,198

[45] Date of Patent: Nov. 10, 1992

[54] METHOD OF USING DEHYDROEPIANDROSTERONE AND DEHYDROEPIANDROSTERONE-SULFATE AS INHIBITORS OF THROMBUXANE PRODUCTION AND PLATELET AGGREGATION

[75] Inventors: David M. Eich; Robert Jesse; John Nestler, all of Richmond, Va.

[73] Assignee: Virginia Commonwealth University, Richmond, Va.

[21] Appl. No.: 765,368

[22] Filed: Sep. 25, 1991

Related U.S. Application Data

[62] Division of Ser. No. 652,518, Feb. 8, 1991, Pat. No. 5,110,810.

[51] Int. Cl.$^5$ .................... A01N 1/02; A61K 31/56
[52] U.S. Cl. ........................ 435/2; 514/178
[58] Field of Search .................... 435/2; 514/178

[56] References Cited

PUBLICATIONS

Jesse, R. et al., J. Am. Coll. Cardiol 17 (2 suppl. A) 1991 376A.

"Human Platelets Modulate Edema Formation In Isolated Rabbit Lungs"; John E. Heffner, James A. Cook and Perry V. Halushka; J. Clin. Invest., 84:757–764 (1989).

"DHEA: Miracle Drug?"; Saul Kent; Geriatrics; 37:157–159 (1982).

"Plasma Dehydroepiandrosterone and Dehydroepiandrosterone Sulfate In Patients Undergoing Diagnostic Coronary Angiography"; D. M. Herrington, G. B. Gordon, S. C. Achuff, J. F. Trejo, H. F. Weisman, P. O. Kwiterovich and T. A. Pearson; J. Amer. Coll. Card., 16:862–870 (1990).

"Inhibition of Mammalian Glucose-6-Phosphate Dehydrogenase by Steroids"; Paul A. Marks and Julia Banks; Proc. Natl. Acad. Sci., 46:447–452 (1960).

"Effect of GSH Depletion by 1-Chloro-2, 4-Dinitrobenzine on Human Platelet Aggregation, Arachidonic Acid Oxidative Metabolism and Cytoskeletal Proteins"; A. Bosia, P. Spangenberg, D. Ghigo, R. Heller, W. Losche, G. P. Pescarmona and U. Till; Thrombosis Research 37; 423–434 (1985).

"Dehydroepiandrosterone Feeding Prevents Aortic Fatty Streak Formation and Cholesterol Accumulation in Cholesterol-Fed Rabbit"; Yadon Arad, Juan J. Badimon, Lina Badimon, Wylie C. Hembree and Henry N. Ginsberg; Arteriosclerosis, 9:159–166 (1989).

"Reduction of Atherosclerosis by Administration of Dehydroepiandrosterone"; Gary B. Gordon, David E. Bush, and Harlan F. Weisman; J. Clin. Invest., 82:712–719 (1988).

"Age Changes and Sex Differences in Serum Dehydroepiandrosterone Sulfate Concentrations throughout Adulthood"; Norman Orentreich, Joel L. Brind, Ronald L. Rizer, and Joseph H. Vogelman; Journal of Clinical Endocrinology and Metabolism; vol. 59, No. 3, pp. 551–555; (1984).

"A Prospective Study of Dehydroepiandrosterone Sulfate, Mortality, and Cardiovascular Disease"; Elizabeth Barrett-Connor, M. D., Key-Tee Khaw, and Samuel S. C. Yen; New Engl. J. Med.; 315:1519–1524 (1986).

Primary Examiner—Douglas W. Robinson
Assistant Examiner—S. Saucier
Attorney, Agent, or Firm—Whitham & Marhoefer

[57] ABSTRACT

Treating human beings with pharmacological quantities of DHEA results in their blood having increased serum DHEA and DHEA-S and lower rates of platelet aggregation. Reducing the rate of platelet aggregation can significantly reduce the incidence of morbidity and mortality from vascular events such as myocardial infarction and stroke, as well as reduce the occurrence of restenosis following vascular interventions. The concentration of DHEA and DHEA-S in the blood and the pre-incubation time of DHEA and DHEA-S with the blood will affect its impact on platelet aggregation. Hence, prior treatment of patients who are at risk with DHEA may produce the most beneficial affects. In addition, treatment of blood with DHEA-S reduces thromboxane production. Thromboxane is produced after platelets are subjected to many different types of agonists and is responsible for recruiting other platelets to aggregate and form a thrombus; therefore, blocking the production of thromboxane will reduce or prevent platelet aggregation.

5 Claims, 5 Drawing Sheets

METHOD OF USING DEHYDROEPIANDROSTERONE AND DEHYDROEPIANDROSTERONE-SULFATE AS INHIBITORS OF THROMBUXANE PRODUCTION AND PLATELET AGGREGATION

This application is a division of copending application Ser. No. 07/652,518, filed on Feb. 8, 1991, now U.S. Pat. No. 5,110,810.

BACKGROUND OF THE INVENTION

1. Field of the Invention

The present invention is generally related to the treatment of human beings with pharmacological quantities of hormones and, more particularly, to the use of dehydroepiandrosterone (DHEA) as an inhibitor of platelet function.

2. Description of the Prior Art

Platelets are the blood cells which are instrumental in stopping bleeding when the integrity of a blood vessel is compromised. Normal blood vessels are lined with a single layer of cells called the endothelium. The endothelium regulates vascular tone and prevents platelets from sticking to blood vessel walls. When the endothelial barrier is disrupted, platelets adhere to sub-endothelial components where they become "activated" and elaborate a number of biologically active compounds. One compound produced after the platelets are "activated" is thromboxane $A_2$ which serves the function of recruiting other platelets to aggregate and form a tight plug called a thrombus. When a vessel has been lacerated, the process of platelet aggregation and thrombus formation serves the beneficial function of stopping the bleeding and allowing time for repair However, if a thrombus forms in the lumen of an intact vessel, the blood flow to tissues subserved by the thrombus becomes compromised and cell death results.

Vascular injury and, in particular, endothelial damage can be caused by many mechanisms. For example, disease processes such as diabetes, hypertension, hyperlipidemia, oxidant injury, and cigarette smoking are known to cause endothelial damage. In addition, endothelial damage can occur iatrogenically (by the actions of a physician) through the use of intravascular remodeling devices such as by balloon angioplasty, atherectomy, or laser surgery. Platelets adhere to areas where the endothelial barrier has been disrupted, and even if an occlusive thrombus does not result when platelets aggregate at the disruption site, the platelets still elaborate compounds thought to be directed toward the repair process such as growth and chemotactic factors which are themselves thought to be important in atherogenesis. Hence, platelet function is thought to play an important role in the generation of atherosclerotic plaques and the events leading to restenosis following mechanical remodeling. It is widely thought that ruptured atherosclerotic plaque is the substrate upon which an acute occlusive thrombus is formed. Intra-coronary thrombosis is the primary etiology of myocardial infarction and stroke.

Platelet function includes a wide variety of platelet activities including among others aggregation, adhesion, and thromboxane production. At present there is a need to find agents capable of attenuating certain platelet activities. Inhibition of platelets could reduce the risk of atherosclerosis, heart attack, stroke, and restenosis following intravascular remodeling procedures. Preferably, suitable agents would not disrupt the ability to stop bleeding in the event of an injury and would not have significant side effects, but would be able to attenuate the deleterious effects of platelets in the disease processes noted above.

While platelets can be activated by a number of biological compounds, many times activation involves a common final pathway which includes the generation of thromboxane $A_2$. As pointed out above, thromboxane $A_2$ is instrumental in platelet aggregation and thrombus formation. Thromboxane $A_2$ is one of the most potent platelet activators known. In addition, thromboxane $A_2$ is a potent vasoconstrictor. Thus, one mechanism for inhibiting platelet aggregation is to block thromboxane formation. Aspirin is the most widely used drug for inhibiting thromboxane formation and preventing subsequent platelet aggregation. In fact, in large clinical studies aspirin has been shown to reduce the incidence of myocardial infarction. However, aspirin does not inhibit initial platelet adhesion or affect elaboration of compounds such as growth factors which are involved in restenosis. Moreover, aspirin does not appear to have an affect on the platelet's role in atherogenesis.

DHEA is an endogenous androgenic steroid which has been shown to have a myriad of biological activities. In U.S. Pat. No. 4,920,115 to Nestler et al., DHEA was shown to reduce body fat mass, increase muscle mass, lower LDL cholesterol levels without affecting HDL cholesterol levels, lower serum apilipoprotein B levels, and not affect tissue sensitivity to insulin in human patients. In Geriatrics 37:157 (1982), DHEA was reported to be a "miracle drug" which may prevent obesity, aging, diabetes mellitus and heart disease. DHEA was widely prescribed as a drug treatment for many years; however, the Food and Drug Administration recently restricted its use. DHEA is readily interconvertible with its sulfate ester DHEA-S through the action of intracellular sulfatases.

Peak serum DHEA and DHEA-S levels occur when a patient is approximately twenty five years old and decline over the ensuing decades. In Ohrentreich et al., J. Clin. Endocrinol. Metab. 59:551–555 (1984), the mean DHEA-S levels and ranges for adult men and women were characterized. For example, in men the means were reported to be as follows: age 25–29=3320 ng/ml, age 45–49=1910 ng/ml, and at age 65–69=830 ng/ml. Similar age related declines in serum DHEA-S levels were found to occur in women. Correspondingly, the incidence of cardiovascular disease in human beings increases with age, thus suggesting an epidemiological relationship between serum DHEA and DHEA-S levels and cardiovascular disease. In Barrett-Conner et al., N. Engl. J. Med. 315:1519–1524 (1986), the baseline DHEA-S levels of 242 middle aged men (ages ranging between 50 and 79 years) was compared to the subsequent 12 year mortality rate of the men from any cause, from cardiovascular disease, and from ischemic heart disease. DHEA-S levels were significantly lower in men with a history of heart disease compared to those without. In men with no history of heart disease, the age-adjusted relative risk associated with DHEA-S levels below 140 $\mu$g/dL was 1.5 (p NS) for death from any cause, 3.3 (p<·0.05) for death from cardiovascular disease, and 3.2 (p<0.05) for death from ischemic heart disease. An increase in DHEA-S level of 100 $\mu$g/dL had a 48% reduction in mortality (adjusted for other risk factors) from cardiovascular disease (p <0.05).

Recently, some studies have suggested that DHEA may have anti-atherosclerotic activity and perhaps acts as an anti-proliferative agent. In particular, Arad et al. in *Arteriosclerosis* 9:159–166 (1989) and Gordon et al. in *J. Clin. Invest.* 82:712–719 (1988) both describe the reduction of atherosclerotic plaque formation by DHEA. In Arad et al., rabbits were fed 0.5% cholesterol and 0.5% DHEA. The extent to the aortic surface covered by fatty streaks was evaluated after two months. Arad et al. observed a 30 or 40% reduction in fatty streak formation as determined by chemical analysis or planimetry of the lesions, respectively. In Gordon et al., rabbits were fed a 2% cholesterol diet and had arterial injury induced by balloon abrasion. One group was fed 0.5% DHEA, and that group had a 50% reduction in plaque size compared with the rabbits not receiving DHEA. The individual reduction of plaque size was inversely proportional to the serum level of DHEA attained, and was not attributable to differences in body weight gain, food intake, total plasma cholesterol or distribution of cholesterol among the VLDL, LDL, or HDL fractions. Neither Arad et al. nor Gordòn et al. made any assessment of the platelet function in their studies and did not hypothesize that alteration in platelet reactivity might have contributed to their findings. Moreover, the data in Arad et al, and Gordon et al. would not support drawing such a conclusion.

In Marks et al., *Proc. Natl. Acad. Sci.* 46:447–452 (1960), it was reported that DHEA was a specific inhibitor of the enzyme glucose-6-phosphate dehydrogenase which is a proximal enzyme in the hexose monophosphate shunt pathway (HMPS). The HMPS pathway is crucial for generating reducing equivalents, such as the reduced form of β-Nicotinamide Adenine Dinucleotide Phoshphate (NADPH), which are vital to many cellular functions. Marks et al. commented that, with the resulting decrease in NADPH production, inhibiting glucose-6-phosphate dehydrogenase could be a means for regulating steroid and cholesterol biosynthesis.

Another consequence of decreased NADPH production by inhibition of glucose-6-phosphate dehydrogenase is that platelets and other affected cells will have a diminished ability to protect against oxidant damage since they do not have the NADPH required to regenerate reduced glutathione (GSH). Bosia et al. in *Thromb. Res.* 37:423–434 (1985) examined the consequences of GSH content on platelets using 1-chloro-3,5-dinitrobenzene (CDNB) which chemically depletes GSH resulting in an effect similar to that induced by blocking the enzymatic regeneration of GHS by DHEA. Bosia et al. found that platelets with depleted GSH levels aggregate normally at higher inducer concentrations, have increased or depressed aggregation at low inducer concentrations depending on the inducer, have faster cytoskeletal protein oxidative polymerization but reversible aggregation, do not stimulate the HMPS pathway (the pathway inhibited by DHEA), and are more sensitive to oxidants. Bosia et al. concluded that GSH is a necessary cofactor for platelet thromboxane synthesis and pointed out that similar effects are seen when DHEA is depleted with diamide or in the case of glucose-6-phosphate dehydrogenase deficient cells.

Heffner et al., in *J. Clin. Invest.,* 84:757–764 (1989), disclosed the ability of platelets to attenuate oxidant induced injury in an isolated lung model. Isolated rabbit lungs were perfused with a physiological buffer containing xanthine and xanthine oxidase, a superoxide-peroxide generating system, which resulted in lung damage as measured by the occurrence of lung edema and acute pulmonary hypertension. Inclusion of intact functioning platelets in the perfusate attenuated the injury. Pretreatment of the platelets with DHEA to inhibit glucose-6-phosphate dehydrogenase resulted in augmentation of the lung edema and pulmonary hypertension. Heffner et al. hypothesized that DHEA interfered with antioxidant activity of platelets by blunting the ability to regenerate reduced glutathione. Heffner et al. reported that thromboxane $B_2$ production was unchanged.

One problem with the Heffner et al. study is that the lungs were perfused with a buffer±platelets solution when, in whole blood, the major oxidant activity resides in the red blood cells and in serum enzymes such as superoxide dismutase. Heffner et al. failed to include such an enzymatic scavenger of superoxide in their controls. The major assessment of lung injury used by Heffner et al. was the measured capillary leak (lung edema). The presence of platelets in the perfusate may attenuate edema by "plugging" capillary leaks. Hence, Heffner et als. hypothesis that DHEA interferes with platelet antioxidant activity by blunting the regeneration of reduced glutathione may be incorrect since DHEA inhibiting the platelet's ability to plug capillary leaks could also explain their results.

SUMMARY OF THE INVENTION

It is therefore an object of this invention to provide a method for inhibiting or reducing the rate of platelet aggregation.

It is another object of this invention to provide a method for reducing the production of thromboxane.

It is yet another object of this invention to treat or prevent such disorders as atherosclerosis, angina, and restenosis after surgery by administering pharmacological quantities of DHEA or DHEA-S to human patients.

According to the invention, pharmacological quantities of DHEA and DHEA-S have been found to reduce the rate of platelet aggregation and thromboxane production.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
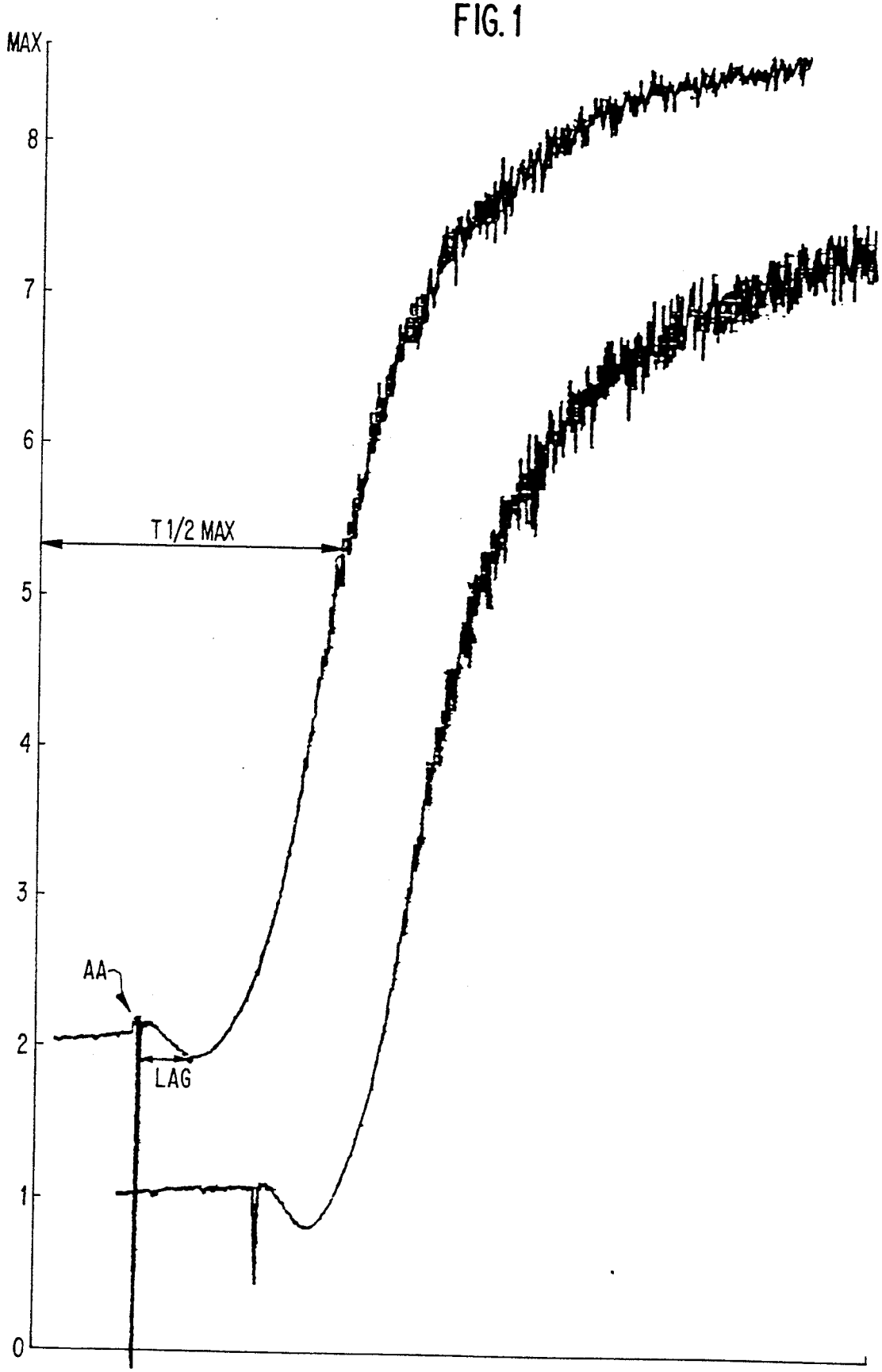
FIG. 1 is a graph showing a sample tracing obtained from an aggregometer.

Referring now to the drawings and, more particularly to FIG. 1, two sample aggregometer tracings are shown which help illustrate the methods used by the inventors to analyze turbidimetric data. Aggregometers are well known research tools and the aggregometer used in the experiments discussed below was a Sienco dual chamber platelet aggregometer. A blood sample which is to be analyzed is drawn from volunteer donors into a $\frac{1}{6}$ volume of acid-citrate-dextrose (an anticoagulant used to keep platelets from aggregation during preparative stages). For the in vitro experiments discussed below, the volunteer donors had not taken any medication for ten days prior to submitting the blood sample. The blood is then centrifuged at low speed to sediment red and white blood cells, leaving a fraction enriched in platelets called platelet-rich plasma (PRP). The platelet count was determined electronically using a Coulter counter. The final concentration of platelets for a test sample was adjusted to 250,000 platelets/$\mu$L fluid by the addition of platelet-poor plasma. The test sample was then stored in a capped syringe for the duration of the experiment which does not exceed four hours from the time of phlebotomy.

The aggregometer acts essentially like a spectrophotometer to measure the turbidity of the platelet suspension as a function of the change in light transmission recorded over time. Prior to making turbidimetric measurements, the test samples were heated to 37° C. (body temperature) and stirred at a constant rate. Inhibitors and/or agonists are added to the test sample in very small quantities so as to minimize the dilutional effect. An important object of the present invention was showing that DHEA and DHEA-S are inhibitors of platelet aggregation. Arachidonic acid, available from Biodata Corp of Hatboro, Pa., is a well known agonist of platelets (i.e., the addition of arachidonic acid to platelets causes aggregation). In the experiments, DHEA and DHEA-S were added to the test sample prior to adding the arachidonic acid so that the platelets could be mixed with the inhibitor before any aggregation initiation caused by the arachidonic acid agonist occurred. Typically, 0.2–0.4 mM arachidonic acid was used to start platelet aggregation.

The aggregometer was calibrated such that the test samples, which contained 250,000 platelets/$\mu$l fluid, allowed 0% light transmission while Platelet Poor Plasma, which is essentially devoid of platelets, allowed 100% light transmission. As shown in FIG. 1, after the addition of arachidonic acid, the platelets first undergo a shape change resulting in a net decrease in light transmission. The time to the nadir in the aggregometer tracing is called the "LAG" time. After the LAG time has passed, the platelets undergo a rapid phase of aggregation. As shown in FIG. 1, while larger and larger aggregates form, more and more light is transmitted, which is reflected by a sharp rise in the aggregometer tracing, until a maximum (MAX) is obtained.

The overall rate of aggregation is determined in part by the LAG time and in part by the rate of the rapid aggregation phase. While the LAG time can easily be determined from the turbidimetric spectra, the rate of rapid aggregation phase is reflection of the overall rate of aggregation is the time to reach $\frac{1}{2}$ maximal aggregation, which is shown on FIG. 1 as T$\frac{1}{2}$MAX for the left-most aggregometer tracing. Therefore, the experiments discussed below have primarily utilized the T$\frac{1}{2}$MAX measurement to quantitatively analyze the affect of DHEA and DHEA-S as platelet aggregation inhibitors.

In vivo experimentation has been conducted with DHEA using a test group of ten male human being subjects. The in vivo experimentation comprised a double blind placebo controlled trial where ten normal male volunteers whose ages ranged between 22 and 37 years old were randomly divided into two five membered groups where the average age for each group was 25 years. In the in vivo experiment, the DHEA group received 300 mg of DHEA per day in the form of 100 mg capsules taken orally three times a day. The placebo group took placebo capsules which looked identical to the capsules containing DHEA three times a day. The DHEA and placebo capsules were prepared by the investigational pharmacy at the Medical College of Virginia and the code identifying which patients took DHEA and which took placebo was maintained by the pharmacy until the study was completed such that neither the patients nor the investigators were aware of who was taking DHEA or placebo. Each of the participants in the trial were told not to alter their lifestyles for the duration of the study and at the conclusion of the experiment each participant said that he had not done so. The human study was approved in advance by the Committee on the Conduct of Human Research at Virginia Commonwealth University/Medical College of Virginia.

Figure 2:
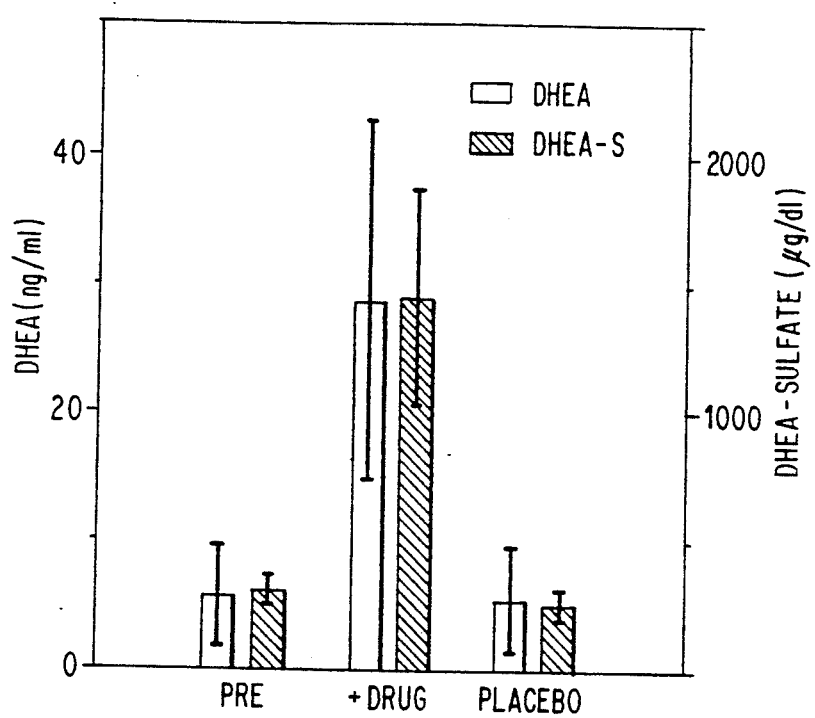
FIG. 2 is a bar graph showing the changes in serum DHEA and DHEA-S levels for the test group receiving supplemental DHEA and the test group receiving placebo found during the second week of the investigation.

Serum DHEA and DHEA-S levels for the patients was determined before the experiment began and at several later times during the experiment. Serum DHEA and DHEA-S testing was performed using radioimmunoassay (RIA) kits purchased from Diagnostic Products, Corp. of Calif. FIG. 2 shows that the mean serum DHEA and DHEA-S levels for the DHEA group increased substantially during the second week (a time when the levels of DHEA in the DHEA group would have reached steady state). Specifically, the baseline serum DHEA, which is identified on FIG. 2 as "PRE" and reflects the mean serum DHEA level for all participants prior to conducting the experiment, was 5.83±3.9 ng/ml, the mean serum DHEA during the second week of investigation for the placebo group was 5.58±4.1 ng/ml, and the mean serum DHEA for the treated group during the second week of investigation was 28.7±13.9 ng/ml. In addition, the baseline serum DHEA-S was 316.2 $\mu$g/dl and during the second week, the mean serum DHEA-S level was 260.5±56.7 $\mu$g/dl in the placebo group and 1451.9±56.7 $\mu$g/dl in the DHEA group. The elevation of serum DHEA and DHEA-S levels in patients receiving supplemental DHEA confirms studies by other investigators and the study reported in U.S. Pat. No. 4,920,115 to Nestler et al. Elevation of serum DHEA-S levels when a patient is receiving only supplemental DHEA suggests that DHEA-S serves as a storage pool for DHEA, which is the active form of the hormone.

In the in vivo experiment, the rate of platelet aggregation for the human subjects participating in the study was examined using turbidimetric techniques as described above in conjunction with FIG. 1 where the T$\frac{1}{2}$MAX and LAG parameters for arachidonic acid induced platelet aggregation were determined. For each subject participating in the experiment, baseline values for T½MAX and LAG were determined on three occasions prior to the start of the investigation and these values were averaged. Then, blood platelet aggregation was again tested on three different occasions during the second week of investigation and these values were also averaged. Finally, the blood platelet aggregation was tested once two weeks after the completion of the investigation (two weeks after being on DHEA or placebo). Performance of the aggregation tests involved making platetet rich plasma test samples as described above and determining the T½Max and lag times for several concentrations of arachidonic acid.

Figure 3:
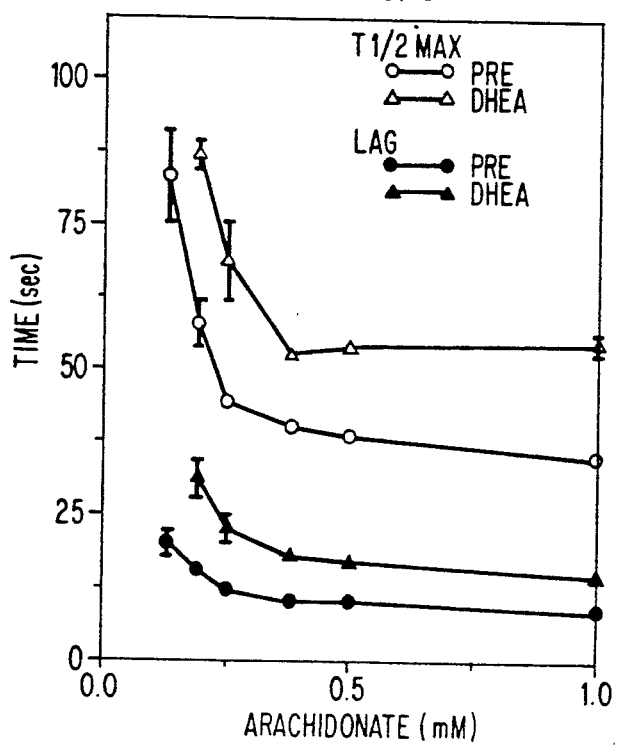
FIG. 3 is a line graph showing that the time to one half the maximum light transmission and lag time curves for one patient were shifted to the right and upward after 7–10 days of receiving the supplemental DHEA.

FIG. 3 shows the T½Max and LAG values for one of the DHEA treated patients at baseline and again during the second week. Each aggregation test was performed in triplicate, thus each data point shown in FIG. 3 is the average of nine data points (as pointed out above, the data points represent the average of three separate testing periods before the investigation began and during the second week of the investigation). In FIG. 3, both the T½MAX and LAG curves are shifted to the right and upward. This translates into a slower rate of aggregation and a requirement for a higher concentration of arachidonic acid to initiate aggregation. Thus, the elevated serum DHEA levels slowed platelet aggregation even when subjected to higher concentrations of agonists, making them much less likely to aggregate.

During the investigation, four of the five patients taking DHEA developed a delay in the rate of aggregation or an increase in the minimal concentration of arachidonic acid required to initiate aggregation: in one of these subjects, arachidonic acid induced platelet aggregation was completely inhibited. In the fifth DHEA patient there was no change. No significant change was observed in the rate of aggregation or concentration of arachidonic acid required to initiate aggregation for any of the subjects which received placebo. It is not clear why one particular patient who received regular doses of DHEA would show a complete inhibition of arachidonic acid induced platelet aggregation while another patient who received the same treatment would show no response to the treatment; however, it has been found that there is an inherent variability in the baseline response among different donors, and this may influence their propensity to be affected by DHEA. It is notable that all the participants in the study were fairly young, and as such had high endogenous DHEA levels. A similar study in elderly patients with relatively low endogenous DHEA may have shown a more dramatic response. Regardless, even in a fairly young study population the inventors were able to demonstrate a reduction in platelet aggregation response by treatment with DHEA.

In vitro turbidimetric experiments were also conducted which show that DHEA and DHEA-S inhibit platelet aggregation. DHEA-S is available from the Sigma Chemical Company in powder form. In the in vitro experiments, blood samples were taken from several young healthy donors taking no medications. Platelet rich plasma was prepared as described above for each test sample and the concentration of platelets in the test samples was adjusted to 250,000 platelets/$\mu$l fluid. Aggregation of the platelets in the test samples was initiated with 0.2 to 0.4 mg of arachidonic acid (there was a variability in the amount of arachidonic acid used among donors; however, the amount used was near the minimum that would consistently initiate aggregation). In all aggregation experiments 0.3 cc of platelet rich plasma was used and the test sample volume placed in the aggregometer ranged between 10 $\mu$l to 30 $\mu$l.

Figure 4:
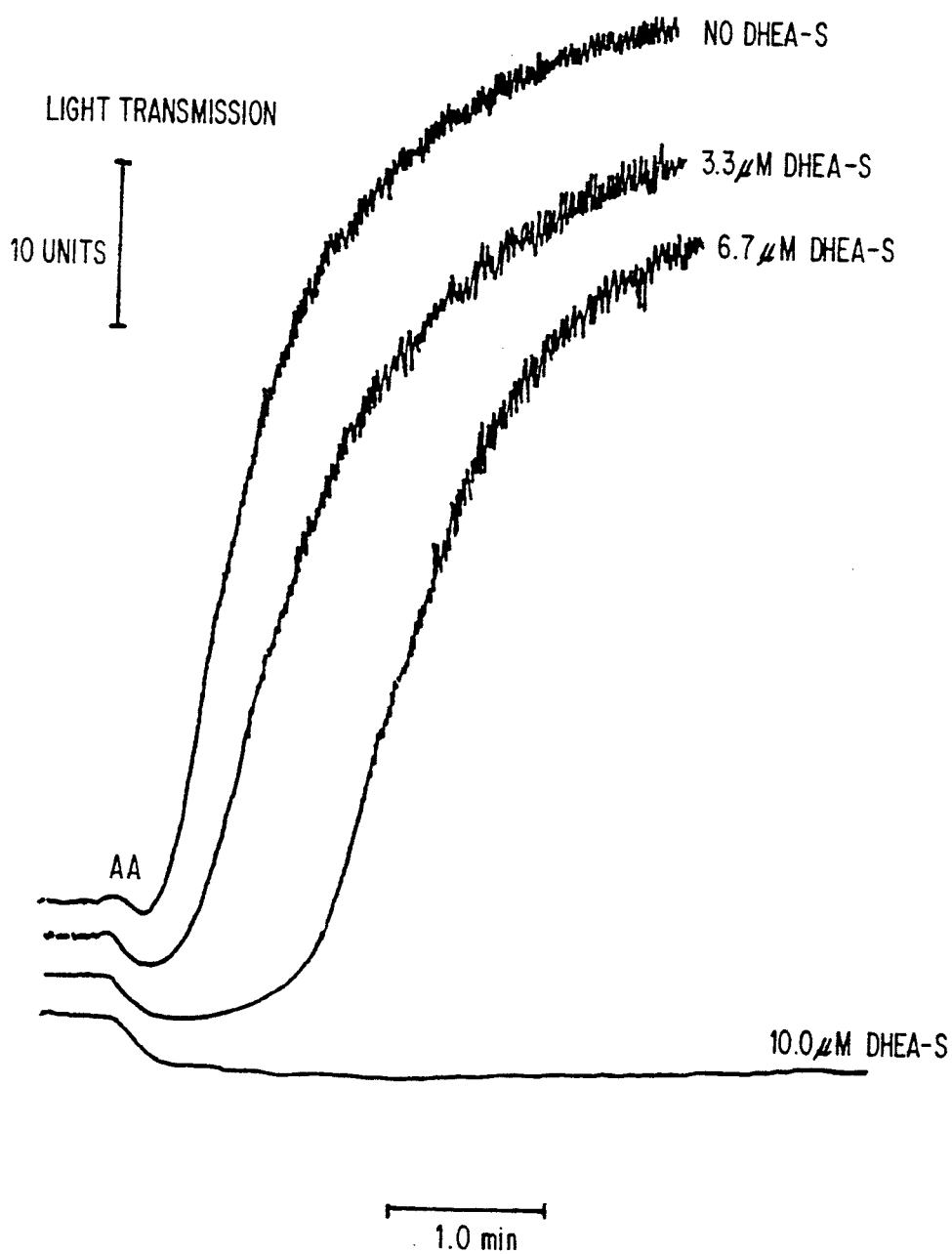
FIG. 4 is a graph showing four aggregometer tracings which illustrate the DHEA-S dose dependent inhibition of arachidonic acid induced platelet aggregation.

In the first in vitro experiment, different concentrations of DHEA-S were added to test samples and the rate of aggregation was monitored after the addition of arachidonic acid. The test samples were incubated with the DHEA-S for three minutes prior to the addition of arachidonic acid. The inventors noted that there was a dose dependent response for platelet aggregation in most test samples which were examined. For example, FIG. 4 shows four aggregometer tracings obtained from one test sample placed adjacent one another where increasing concentrations of DHEA-S were utilized. The T½MAX and LAG times increase with increasing concentrations of DHEA-S. In fact, at 10.0 $\mu$M DHEA-S, the time for T½MAX and LAG was not determinable. Hence, subjecting platelets to increasing concentrations of DHEA-S results in a reduction in the rate of aggregation of the platelets.

Figure 5:
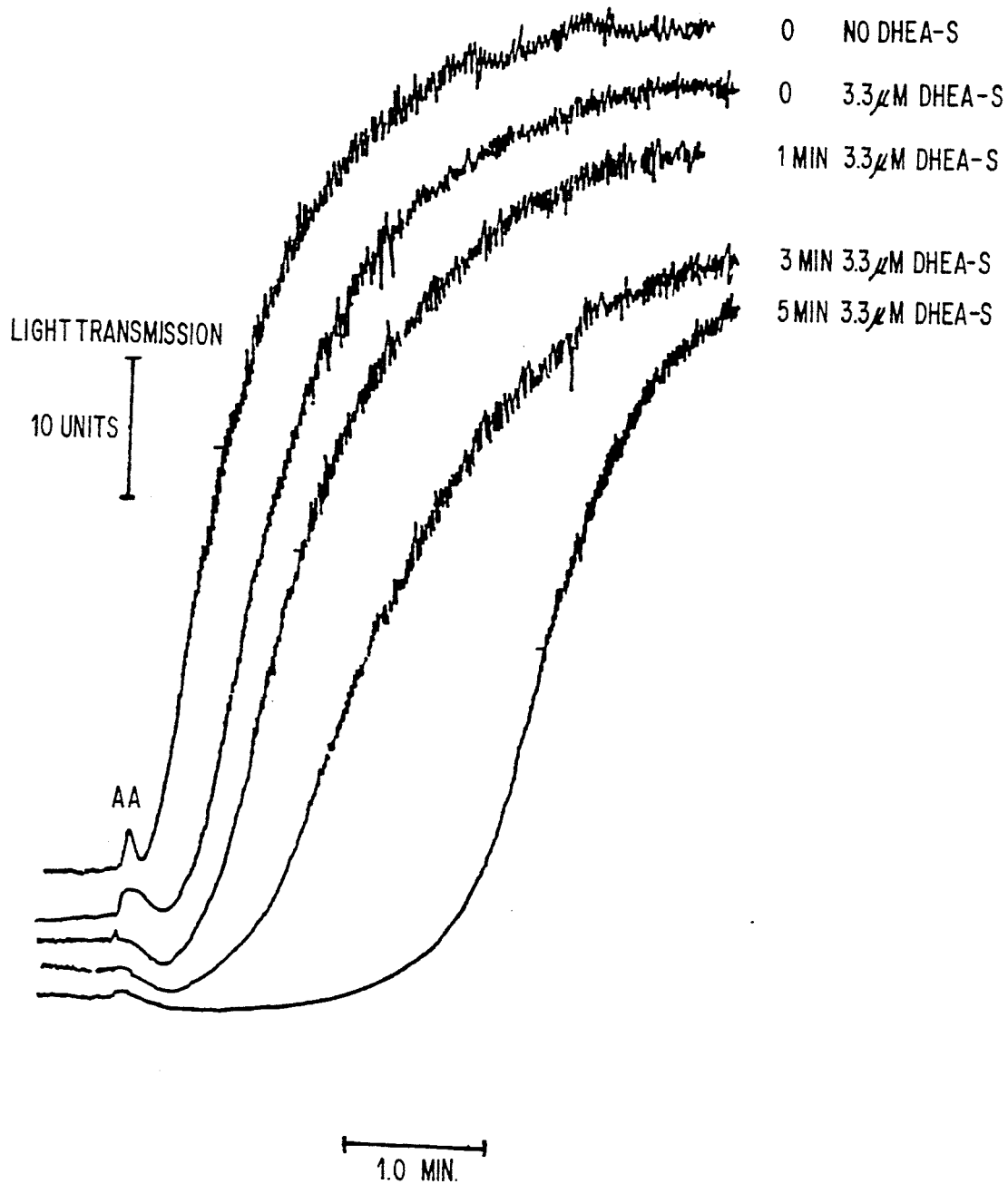
FIG. 5 is a graph showing five aggregometer tracings which illustrate the pre-incubation time dependent inhibition of arachidonic acid induced platelet aggregation for platelets treated with DHEA.

In the second in vitro experiment, platelet rich plasma test samples were placed in aggregometer cuvettes, 3.3$\mu$M DHEA-S was added to the samples, the samples with added DHEA-S were then incubated in the aggregometer for a specified period of time, and then 0.2-0.4 mg of arachidonic acid was added to the samples and platelet aggregation was monitored with the aggregometer. As will be discussed in more detail below, the inventors noted that the rate of platelet aggregation was also dependent on the amount of time the platelets were pre-incubated. For example, FIG. 5 shows five adjacent aggregometer tracings for platelet fractions taken from the same test sample. It is interesting to note that simply adding DHEA-S and adding arachidonic acid immediately thereafter did increase the T½MAX and LAG from baseline (this is indicated as no DHEA-S at 0 time and 3.3 $\mu$M DHEA-S at 0 time). Hence, it does not take very much time for the presence of DHEA-S to have an impact on platelet aggregation. More importantly from FIG. 5, it can be seen that the longer the pre-incubation time, the greater the increase in T½MAX and LAG times. This suggests that treating patients on a daily basis, where the platelets would be continually mixed with the supplemental amounts of DHEA or DHEA-S, would have the greatest impact on the reduction in the rate of platelet aggregation. Hence, daily treatment with DHEA or DHEA-S for the treatment or prevention of atherosclerosis, restenosis after surgery, or similar disorders may be preferred.

Figure 6:
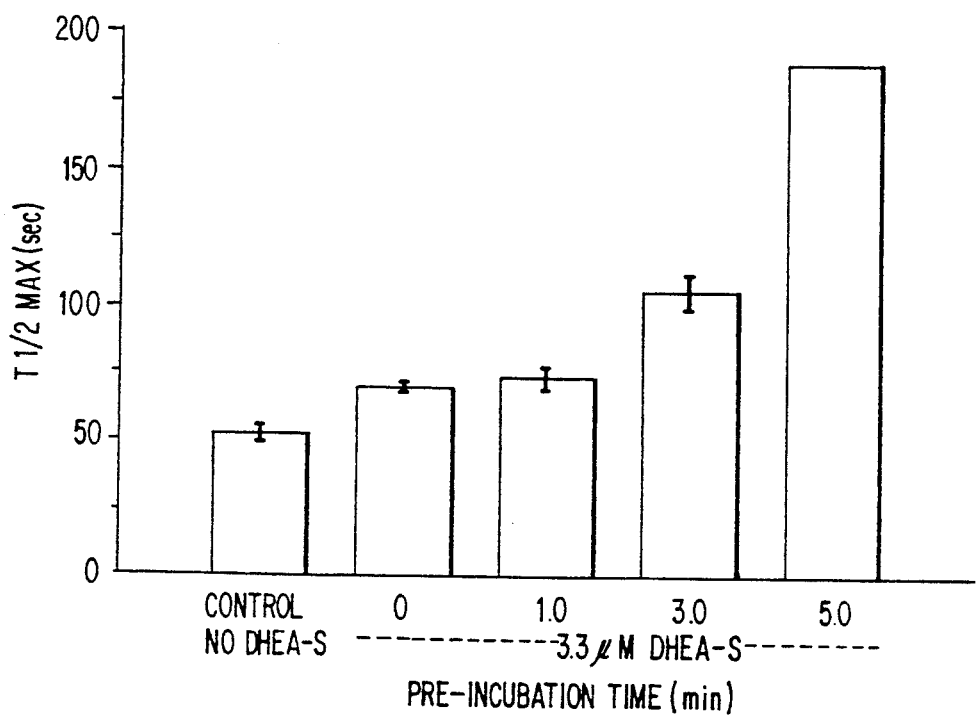
FIG. 6 is a bar graph showing the effect of pre-incubation times on arachidonic acid induced platelet aggregation for platelets treated with DHEAS.

FIG. 6 shows the T½MAX for varying pre-incubation time periods for test samples treated with 3.3 $\mu$M of DHEA-S. The T½MAX values were derived from the aggregation curves from several experiments with different donors. All data points are the sum of at least six determinations with the exception of the 5.0 minute time point which in most cases resulted in complete inhibition of aggregation. The error bars represent standard errors from the mean. As discussed in conjunction with FIG. 5, for each data bar in FIG. 6 the test sample was pre-incubated with DHEA-S for the noted period of time prior to initiation of aggregation by arachidonic acid. The control bar is the T½MAX for test samples which did not receive any DHEA-S prior to initiation of aggregation with arachidonic acid. The 0 time point represents data from tests where the sample was treated with arachidonic acid immediately after the addition of DHEA-S (i.e., approximately five seconds) and the remainder are pre-incubation times of 1.0, 3.0, and 5.0 minutes, respectively. The data in FIG. 6 indicate that pre-incubation with DHEA can prolong and eventually inhibit platelet aggregation. There appears to be a short time delay required for equilibration of DHEA with the platelets before the full effect is observed.

Figure 7:
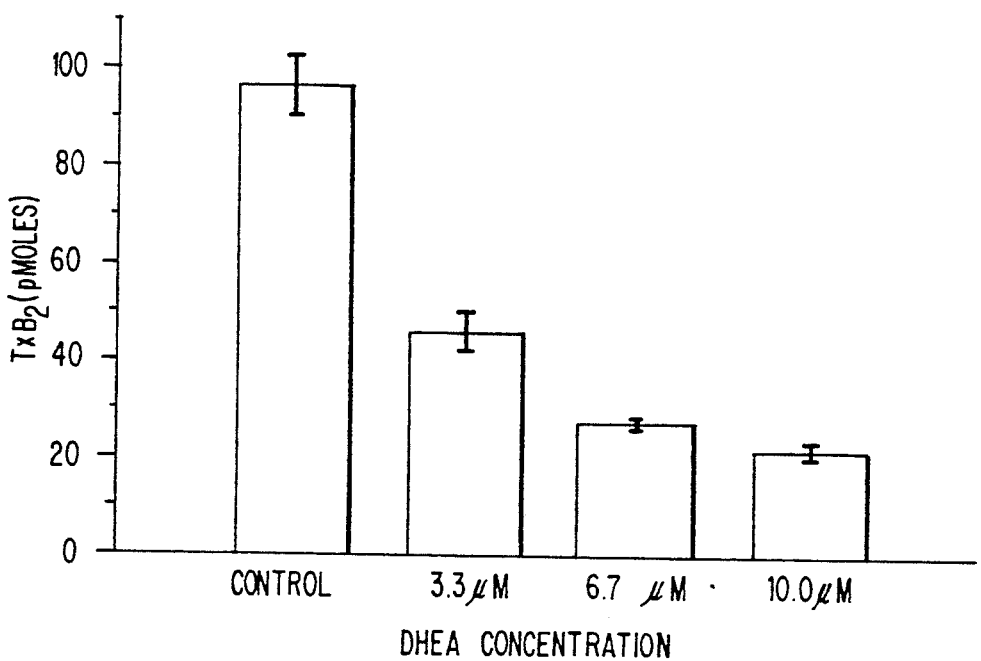
FIG. 7 is a bar graph showing the effect of increasing concentrations of DHEA on thromboxane production in platelet rich plasma.

As discussed above, activation of platelets by arachidonic acid typically results in the generation of Thromboxane A2 ($TxA_2$). The extent of $TxA_2$ generated can be measured by radioimmunoassay (RIA) of its stable breakdown product Thromboxane B2($TxB_2$) (see, JW Aiken, "Arachidonic Acid Metabolism and the Cardiovascular System" in *Platelets and Prostaglandins in Cardiovascular Disease*, J Mehta, P Mehta eds. Futura Publishing Co., Mt. Kisco, NY 1981). FIG. 7 shows the results of an experiment where test samples, prepared as described above where each sample contained 250,000 platelets/$\mu$l fluid and had a total volume of 0.3 cc, were incubated for a brief time period (approximately three minutes) with increasing concentrations of DHEA and aggregation was initiated with arachidonic acid. The platelet aggregation reaction was terminated at maximal aggregation or at four minutes, which ever occurred last, by the addition of 10 $\mu$M Indomethacin and 5.0 mM ethylenediaminetetraacetic acid (EDTA). Indomethacin and EDTA are commercially available reagents and were obtained from the Sigma Chemical Company. After adding the Indomethacin and EDTA reagents, the cuvettes containing the test sample were immediately placed on ice to cool. The test samples were then spun at a high speed in an Epindorf, Model 5415 micro-centrifuge, available from Brinkman Instruments, to sediment the platelets. Afterwards, plasma was removed from each sample. The $TXB_2$ content was then assayed using commercial RIA kits available from Advanced Magnetics, Inc. of Mass. As is shown in FIG. 7, there was a proportional decline in $TxB_2$ produced depending on the concentration of DHEA added. Specifically, the control without DHEA had 96.8±6.2 pg/ml $TXB_2$, the samples treated with 3.3 $\mu$M DHEA had an average of 46.0±4.0 pg/ml $TxB_2$ produced, the samples treated with 6.7 $\mu$M DHEA had an average of 27.3±1.1 pg/ml $TXB_2$ produced, and the samples treated with 10.0 $\mu$M DHEA had an average of 21.8±1.8 pg/ml $TXB_2$ produced. Hence, the results in FIG. 7 show that there was a net inhibition of $TxA_2$ synthesis in the presence of added DHEA.

The above reported experimental results show that treating human beings with pharmacological quantities of DHEA can result in their blood having increased serum DHEA and DHEA-S and lower rates of platelet aggregation. Reducing the rate of platelet aggregation can significantly reduce the incidence of morbidity and mortality from vascular events such as myocardial infarction and stroke, as well as reduce the occurrence of restenosis following vascular interventions. It should be understood that DHEA can be administered to patients in ester, salt (e.g., DHEA-S) or other pharmaceutically acceptable form and within binders, elixirs, and other pharmaceutically acceptable mixtures. The dose of DHEA should be based on well known pharmaceutically accepted principles (e.g., preferably 100 to 2000 mg per day which can be taken as a single or multiple doses per day).

The above results also show that the concentration of DHEA and DHEA-S in the blood and the pre-incubation time of DHEA and DHEA-S with the blood will effect its impact on platelet aggregation. Hence, prior treatment of patients who are at risk with DHEA may produce the most beneficial affects. Furthermore, the above results show treatment of blood with DHEA-S will reduce thromboxane production. Thromboxane is produced after platelets are subjected to many different types of agonists and is responsible for recruiting other platelets to aggregate and form a thrombus; therefore, blocking the production of thromboxane will reduce or prevent platelet aggregation While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A method of reducing the production of thromboxane in blood plasma, comprising the steps of determining a thromboxane level in blood plasma and adding an amount of dehydroepiandosterone or dehydroepiandosterone sulfate to said blood plasma effective to reduce said thromboxane level.

2. A method as recited in claim 1 wherein said dehydroepiandosterone sulfate is added as a pharmaceutically acceptable salt.

3. A method as recited in claim 1 wherein said amount comprises 100 milligrams to 2000 milligrams per day of dehydroepiandosterone or dehydroepiandosterone sulfate.

4. A method as recited in claim 3 wherein said amount comprises 300 milligrams per day of dehydroepiandosterone or dehydroepiandosterone sulfate.

5. A method as recited in claim 1 wherein said step of adding is performed in vivo.

* * * * *